United States Patent
Desai et al.

(10) Patent No.: US 6,770,785 B1
(45) Date of Patent: Aug. 3, 2004

(54) ANTIOZONANT CUM ANTIOXIDANT, PROCESS FOR PREPARATION

(75) Inventors: Shrojal Mohitkumar Desai, Pune (IN); Shailendra Singh Solanky, Pune (IN); Raj Pal Singh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,107

(22) Filed: Mar. 25, 2003

(51) Int. Cl.$^7$ ............... C07C 215/74; C07C 213/08
(52) U.S. Cl. ............ 564/355; 564/384; 564/386; 564/389
(58) Field of Search ............... 564/355, 384, 564/386, 389

(56) References Cited

U.S. PATENT DOCUMENTS

| | | | | |
|---|---|---|---|---|
| 4,717,492 A | * | 1/1988 | Chibnik | 508/561 |
| 5,834,544 A | * | 11/1998 | Lin et al. | 524/217 |

* cited by examiner

*Primary Examiner*—Brian Davis
(74) *Attorney, Agent, or Firm*—Ladas & Parry

(57) ABSTRACT

The present invention relates to a novel antiozonant as well as antioxidant based on functionalized hindered phenol and the process for the preparation thereof of formula 1

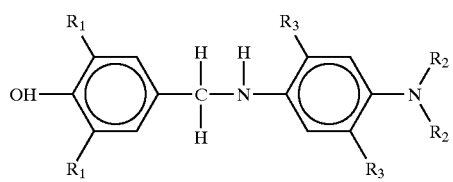

Formula 1 wherein $R_1$ is tert-butyl and $R_2$ and $R_3$ are $C_1$ to $C_8$ linear or branched alkyl. The present invention also relates to a process for the preparation thereof comprising dissolving a compound of formula 3

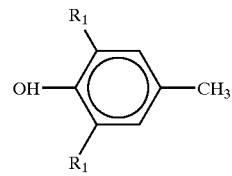

Formula 3 wherein $R_1$ is tert-butyl, with liquid bromine in a non polar organic solvent at temperature range 80 to 95° C. for a period of 4 to 7 hours, evaporating the solvent under reduced pressure to obtain a compound of formula 2

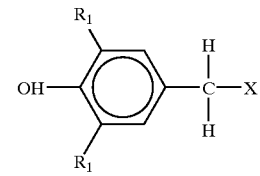

Formula 2 wherein $R_1$ is a tertiary butyl group and X is Br, reacting the compound of formula 2 with a compound of formula 4

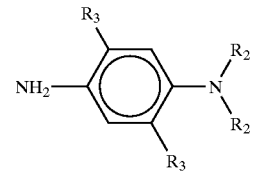

Formula 4 wherein $R_2$ and $R_3$ are $C_1$ to $C_8$ linear or branched alkyl, dissolved in an organic solvent in presence of a suitable mild base at a temperature ranging from 80 to 95° C. for a period of 4 to 7 hours, bringing the reaction mixture to room temperature, separating the organic layer and concentrating the product by solvent evaporation under reduced pressure and purifying the final product by column chromatography to obtain compound of formula 1.

9 Claims, No Drawings

ANTIOZONANT CUM ANTIOXIDANT, PROCESS FOR PREPARATION

FIELD OF THE INVENTION

This invention relates to the preparation of novel antiozonant as well as antioxidant based on functionalized hindered phenol and the process for the preparation thereof. More particularly it relates to the said absorber having a formula 1:

Formula 1

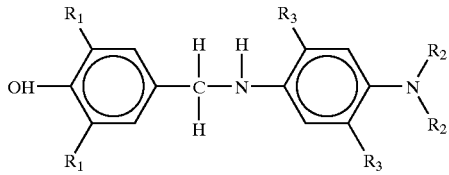

wherein $R_1$ is tert-butyl and $R_2$ and $R_3$ are $C_1$ to $C_8$ linear or branched alkyl. Still more particularly, the invention relates to novel antiozonant as well as antioxidant based on functionalized hindered phenols and useful as condensable monomer for the synthesis of many polymers with in-built antioxidants and the process for the synthesis thereof.

Co-pending application Ser. No. 10/396126 relates to the novel antiozonant as well as antioxidant based on functionalized hindered phenol obtained by the process of this invention.

More particularly the present invention relates to the preparation of said novel antiozonant and antioxidant, using compound of formula 2

Formula 2

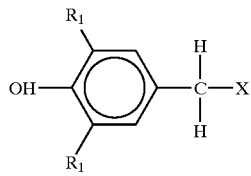

wherein $R_1$ is a tertiary butyl group and X is Br, which is prepared by the halogenation of a hindered phenol of the general Formula 3

Formula (3)

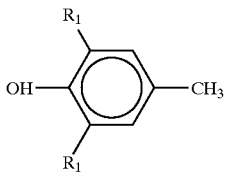

wherein $R_1$ is tert-butyl with a compound having general Formula 4

Formula (4)

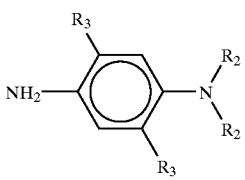

wherein $R_2$ and $R_3$ are $C_1$ to $C_8$ linear or branched alkyl.

BACKGROUND OF THE INVENTION

Hindered phenols have been used as stabilizers in foodstuffs, rubber, plastics, oils etc. since long. Polymers have replaced metals, glass, ceramics and papers in packaging, automobiles, building construction, electronics, electrical equipment, furniture, pipes and heavy industrial equipments. In a nutshell, from agriculture to transport and aerospace to food packaging, the use of plastics have become integral parts of our daily life. Polymers, all natural and synthetic, in common use, are susceptible to thermal/photo-oxidative degradation upon exposure to natural and artificial weathering. The deterioration of these polymeric materials is mainly due to the heat and UV portion of sunlight reaching the earth surface. The net result of degradation is the loss in the molecular weight and macroscopic physical properties. In order to avoid this loss, different types of stabilizers have been devised that protect the polymeric substrate from detrimental effect of heat and light.

This invention relates to N,N-di substituted para-phenylene diamines as representing compound of Formula 1 which offer protection to polymers such as natural rubber and elastomers against the deteriorous effects of oxygen and ozone. It also relates to the methods for the preparation and use of these materials and to the compositions formed by mixing these materials with polymers. Para-phenylene diamines have been used as antioxidants and antiozonants since long.

Following patents and literature provide information about synthesis of the antioxidants and antiozonants and their uses. For example, U.S. Pat. No. 3,644,482 describes hindered phenol stabilizers based on esters of 3-(3,5-di-t-butyl4-hydroxyphenyl)propionate. N-alkyl, N'-phenyl-p-phenylene diamines are revealed in U.S. Pat. Nos. 3,409,586; 3,424,713; 3,542,691; 3,663,505 and 3,839,275 and British Patent No. 1,035,262. Sulphur containing para-phenylene diamines are disclosed in U.S. Pat. No. 3,035,014. In addition, aromatic amines have also been revealed in U.S. Pat. No. 3,505,225 as antioxidants based on α-methylstyryl-substituted diphenylamines. In addition, U.S. Pat. Nos. 4,797,511 and 4,837,259 describe the synergistic blends of hindered phenols and amine antioxidants as stabilizers for polypropylene and polyethylene. U.S. Pat. No. 3,304,283 discloses an antioxidant composition for mono-olefinic polymers, containing at least one aromatic phenolic thioether, diaryl thioether, aliphatic disulfide, aromatic disulfide and/or aliphatic thiuramdisulfide in combination with at least one biphenol and/or aromatic amine. The mixtures of an amine component and a sterically hindered phenol component with and without other ingredients are also revealed in U.S. Pat. Nos. 3,432,578; 3,567,664; 3,637,865; 3,655,559; 5,834,544 and 5,120,844.

The one step acid catalyzed reaction with thiols, formaldehyde and aromatic amines is known in the prior art (J. Org. Chem., 24, 1035(1959); J. Org. Chem., 28, 2763(1963) and J. Org. Chem., 30, 28(1965). As known to the skilled in the art, degradation of rubber from ozone manifests itself by (i) crack appearing perpendicular to the stress in the rubber and (ii) the appearance of a silvery film on the surface of the article. The attack of ozone is a purely surface phenomenon. The function of the antiozonant depends on migration to the surface of the rubber article.

OBJECTS OF THE INVENTION

The main object of the present invention is therefore, to provide a novel antiozonant as well as antioxidant based on functionalized hindered phenol and a process for the preparation thereof, which can fulfill the prerequisites of a polymer stabilizer and can be synergistically used with other polymer stabilizers. Moreover, this class of combination of hindered phenols and diamines are known to be compatible with polyolefins, polycarbonate, polystyrene and diene-elastomers and can even be added in an additive proportion to obtain desired thermal stability of various other polymers.

SUMMARY OF THE INVENTION

The present invention provides a novel combination of antioxidant and antiozonant based on functionalized hindered phenol of the formula 1

Formula 1

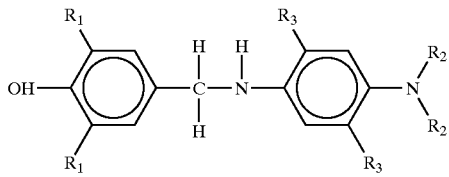

wherein $R_1$ is tert-butyl and $R_2$ and $R_3$ are $C_1$ to $C_8$ linear or branched alkyl.

The present invention also provides a process for the preparation of novel antioxidant cum antiozonant of the formula 1 below Formula 1

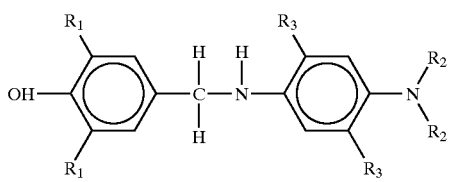

which comprises dissolving a compound of formula 3

Formula 3

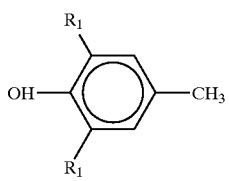

wherein $R_1$ is tert-butyl, with bromine in a non polar organic solvent at a temperature in the range of 80 to 95° C. for a period of 4 to 7 hours, evaporating the solvent under reduced pressure to obtain a compound of formula 2

Formula 2

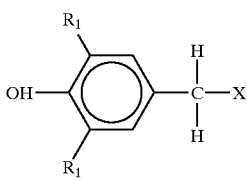

wherein $R_1$ is a tertiary butyl group and X is Br, reacting the compound of general Formula 2 with compound of formula 4

Formula 4

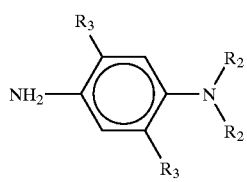

wherein $R_2$ and $R_3$ are $C_1$ to $C_8$ linear or branched alkyl, in presence of an organic solvent using a mild base at a temperature in the range of 80 to 95° C. for a period of 4 to 7 hours, bringing the reaction mixture to room temperature, separating the organic layer and concentrating the product and purifying the final product of formula 1.

In one embodiment of the present invention, the neutral organic solvent used for dissolving the compound of formula 3 is a chlorinated solvent selected from the group consisting of carbon tetrachloride, chloroform, chlorobenzene and dichloromethane.

In another embodiment of the invention, the bromination of compound of formula 3 is achieved by using liquid bromine.

In still another embodiment of the invention, the para-phenylene diamine of formula 4 is selected from N,N-dimethyl-para-phenylene diamine, N,N-diethyl-para-phenylene diamine, 2,5-dimethyl-para-phenylene diamine and 2,5-diethyl-para-phenylene diamine.

In still another embodiment of the invention, the solvent used to dissolve the para-phenylene diamine is tetrahydrofuran (THF).

In still another embodiment of the invention, the inorganic base used to basify para-phenylene diamine is selected from carbonates or bicarbonates of alkali metals such as potassium carbonate, sodium carbonate, potassium bicarbonate and sodium bicarbonate.

In another embodiment of the invention, the product of formula 1 is concentrated by solvent evaporation under reduced pressure and purified by silica gel chromatography.

DETAILED DESCRIPTION OF THE INVENTION

The present invention provides a novel combination of antioxidant and antiozonant based on functionalized hindered phenol of the formula 1

Formula 1

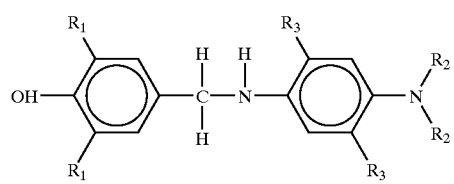

wherein $R_1$ is tert-butyl and $R_2$ and $R_3$ are $C_1$ to $C_8$ linear or branched alkyl.

The novel antioxidant cum antiozonant of the invention is prepared by dissolving a compound of formula 3

Formula 3

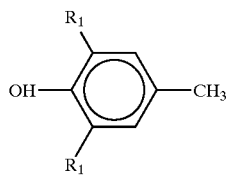

wherein $R_1$ is tert-butyl, with bromine in a non polar organic solvent at a temperature in the range of 80 to 95° C. for a period of 4 to 7 hours, evaporating the solvent under reduced pressure to obtain a compound of formula 2

Formula 2

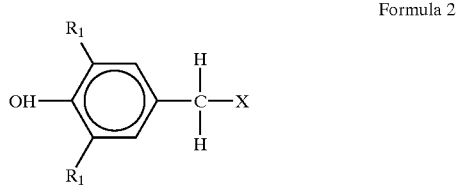

wherein $R_1$ is a tertiary butyl group and X is Br, reacting the compound of general Formula 2 with compound of formula 4

Formula 4

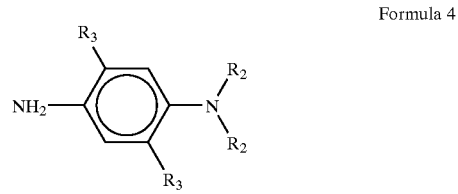

wherein $R_2$ and $R_3$ are $C_1$ to $C_8$ linear or branched alkyl, in presence of an organic solvent using a mild base at a temperature in the range of 80 to 95° C. for a period of 4 to 7 hours, bringing the reaction mixture to room temperature, separating the organic layer and concentrating the product by solvent evaporation under reduced pressure and purifying the final product of formula 1 using silica gel column chromatography.

The neutral organic solvent used for dissolving the compound of formula 3 is a chlorinated solvent selected from the group consisting of carbon tetrachloride, chloroform, chlorobenzene and dichloromethane. Bromination of compound of formula 3 is achieved by using liquid bromine. The para-phenylene diamine of formula 4 is selected from N,N-dimethyl-para-phenylene diamine, N,N-diethyl-para-phenylene diamine, 2,5dimethyl-para-phenylene diamine and 2,5-diethyl-para-phenylene diamine. The solvent used to dissolve the para-phenylene diamine is tetrahydrofuran (THF) while the inorganic base used to basify para-phenylene diamine is selected from carbonates or bi-carbonates of alkali metals such as potassium carbonate, sodium carbonate, potassium bicarbonate and sodium bicarbonate.

The process of the present invention is described herein below with references to examples that are illustrative only and should not be constructed to limit the scope of the present invention in any manner whatsoever.

EXAMPLE 1

Synthesis of 3,5-di-tert-butyl-4-hydroxy benzyl bromide

In a 250 ml three-necked round bottom flask, 2.5 g (0.0113 mol) of 2,6-di-tert-butyl-4-methyl phenol was dissolved in 50 mL of dry carbon tetrachloride. In a separate conical flask 1.83 g (0.589 mL, 0.0115 mol) of bromine was dissolved in 50 mL of dry carbon tetrachloride and solution was transferred to a cylindrical funnel with pressure equalizing tube. Three-necked round-bottom flask containing solution of 2,6-di-tert-butyl-4-methyl phenol was kept in oil-bath at 85° C. Solution in the flask was continuously stirred with the help of magnetic stirrer. Bromine solution was added, drop-by-drop, from funnel to the flask for a span of 4–5 hours till all the solution was poured out. The reaction was terminated after that and the final reaction mixture was allowed to cool at room temperature. The product isolated by solvent evaporation was a viscous yellow liquid and was absolutely pure. The yield of 3,5-di-tert-butyl-4-hydroxy benzyl bromide or 4bromomethyl2,6-di-tert-butyl-phenol was 3.05 g (90%).

EXAMPLE 2

Synthesis of 4-[(4-Amino-phenylamino)-methyl]-2, 6-di-tert-butyl-phenol

4-Bromomethyl-2,6-di-tert-butyl-phenol (2.42 g, 0.008 mole) was dissolved in 50 mL of dry tetrahydrofuran. In a separate conical flask benzene-1,4-diamine (p-PDA) (1.728 g, 0.016 mole) was dissolved in 25 mL of tetrahydrofuran and solution was transferred to a cylindrical funnel with pressure equalizing tube. Three-necked round-bottom flask containing solution of 4-Bromomethyl-2,6-di-tert-butyl-phenol was kept in oil-bath at 85° C. Solution in the flask was continuously stirred with the help of magnetic stirrer. Benzene-1,4-diamine solution was added drop-by-drop, from funnel to the flask in acidic medium for a span of 4–5 hours till all the solution was poured out. The reaction was terminated after that and the final reaction mixture was allowed to attain room temperature. The product was purified using silica gel column chromatography. Product was identified by $^1$H-NMR. The yield of 4-[(4-Amino-phenylamino)-methyl]-2,6-di-tert-butyl-phenol was 2.24 g (85%).

EXAMPLE 3

Synthesis of 2,6-di-tert-butyl-4[(4-dimethylamino-phenylamino)-methyl]-phenol

4-Bromomethyl-2,6-di-tert-butyl-phenol (2.42 g, 0.008 mole) was dissolved in 50 mL of dry tetrahydrofuran. In a separate conical flask N,N-dimethyl-benzene-1,4-diamine (2.17 g, 0.016 mole) was dissolved in 25 mL of tetrahydrofuran and solution was transferred to a cylindrical funnel with pressure equalizing tube. Three-necked round-bottom flask containing solution of 4-Bromomethyl-2,6-di-tert-butyl-phenol was kept in oil-bath at 85° C. Solution in the flask was continuously stirred with the help of magnetic stirrer. N, N-dimethyl-para-phenylene diamine solution was added drop-by-drop, from funnel to the flask in acidic medium for a span of 4–5 hours till all the solution was poured out. The reaction was terminated after that and the final reaction mixture was allowed to attain room temperature.

The product was purified using silica gel column chromatography. Product was identified by $^1$H-NMR. The yield of 2,6-di-tert-butyl-4-[(4-dimethylamino-phenylamino)-methyl]-phenol is 1.80 g (63%).

EXAMPLE 4

Synthesis of 4[(4-Amino-2,5-dimethyl-phenylamino)-2,6-di-tert-butyl-phenol

4-Bromomethyl-2,6-di-tert-butyl-phenol (2.42 g, 0.008 mole) was dissolved in 50 mL of dry tetrahydrofuran. In a separate conical flask 2,5-dimethyl-benzene-1,4-diamine (2.17 g, 0.016 mole) was dissolved in 25 mL of tetrahydrofuran and solution was transferred to a cylindrical funnel with pressure equalizing tube. Three-necked round-bottom flask containing solution of 4-Bromomethyl-2,6-di-tertbutyl-phenol was kept in oil-bath at 85° C. Solution in the flask was continuously stirred with the help of magnetic stirrer. 2,5-dimethyl-para-phenylene diamine solution was added drop-by-drop, from funnel to the flask in acidic medium for a span of 4–5 hours till all the solution was poured out. The reaction was terminated after that and the final reaction mixture was allowed to attain room temperature. Product was separated by solvent evaporation. The product was purified using silica gel column chromatography. Product was identified by $^1$H-NMR. The yield of 4-[(4-Amino-2,5-dimethyl-phenylamino)-2,6di-tert-butyl-phenol is 1.86 g (65%).

EXAMPLE 5

Synthesis of 2,6-di-tert-butyl-4-{[4-(1,4-dimethyl-pentylamino)-phenylamino)methyl}-phenol 4Bromomethyl-2,6-di-tert-butyl-phenol (2.42 g, 0.008 mole) was dissolved in 50 mL of dry tetrahydrofuran. In a separate conical flask N(1,4-Dimethyl-pentyl)-benzene-1,4-diamine (3.28 g, 0.016 mole) was dissolved in 25 mL of tetrahydrofuran and solution was transferred to a cylindrical funnel with pressure equalizing tube. Three-necked round-bottom flask containing solution of 4-Bromomethyl-2,6-di-tert-butyl-phenol was kept in oil-bath at temperature 85° C. Solution in the flask was continuously stirred with the help of magnetic stirrer. N(1,4-Dimethyl-pentyl)-benzene-1, 4diamine solution was added drop-by-drop, from funnel to the flask in acidic medium for a span of 4–5 hours till all the solution was poured out. The reaction was terminated after that and the final reaction mixture was allowed to attain room temperature. Product was separated by solvent evaporation. The product was purified using silica gel column chromatography. Product was identified by $^1$H-NMR. The yield of 2,6-di-tert-butyl-4-{[4-(1,4-dimethyl-pentylamino)-phenylamino)methyl}-phenol is 2. 29 g (67%).

EXAMPLE 6

Synthesis of 2,6di-tert-butyl4-{[(4-phenylamino-phenylamino)-phenol

4-Bromomethyl-2,6-di-tert-butyl-phenol (2.42 g, 0.008 mole) was dissolved in 50 mL of dry tetrahydrofuran . In a separate conical flask N-Phenyl-benzene-1,4-diamine (2.93 g, 0.016 mole) was dissolved in 25 mL of tetrahydrofuran and solution was transferred to a cylindrical funnel with pressure equalizing tube. Three-necked round-bottomed flask containing solution of 4-Bromomethyl-2,6-di-tert-butyl-phenol was kept in oil-bath at 85° C. Solution in the flask was continuously stirred with the help of magnetic stirrer. N-Phenyl-benzene-1,4-diamine solution was added drop-by-drop, from funnel to the flask in acidic medium for a span of 4–5 hours till all the solution was poured out. The reaction was terminated after that and the final reaction mixture was allowed to attain room temperature. Product was separated by solvent evaporation. The product was purified using silica gel column chromatography. Product was identified by $^1$H-NMR. The yield of 2,6-di-tert-butyl-4-[(4-phenylamino-phenylamino)phenol is 2.044 g (63%).

EXAMPLE 7

Synthesis of 2,6-di-tert-butyl4-[(4-isopropylamino-phenylamino)-methyl]-phenol

4-Bromomethyl-2,6-di-tert-butyl-phenol (2.42 g, 0.008 mole) was dissolved in 50 mL of dry tetrahydrofuran. In a separate conical flask N-Isopropyl-benzene-1,4-diamine (2.40 g, 0.016 mole) was dissolved in 25 mL of tetrahydrofuran and solution was transferred to a cylindrical funnel with pressure equalizing tube. Three-necked round-bottomed flask containing solution of 4-Bromomethyl-2, 6di-tert-butyl-phenol was kept in oil-bath at 85° C. Solution in the flask was continuously stirred with the help of magnetic stirrer. N-Isopropyl-benzene-1,4-diamine solution was added drop-by-drop, from funnel to the flask in acidic medium for a span of 4–5 hours till all the solution was poured out. The reaction was terminated after that and the final reaction mixture was allowed to attain room temperature. The product was purified using silica gel column chromatography. Product was identified by $^1$H-NMR. The yield of 2,6di-tert-butyl4-[(4isopropylamino-phenylamino) methyl]-phenol is 2.025 g (68%).

The process of the present invention has four distinct merits:
1) Bromination of hindered phenol does not involve use of any radical initiator or catalyst.
2) The process is economic and gives high yield ($\geq 63\%$) of product.
3) The process comprises of commonly available organic reagents and mild reaction conditions.
4) Reaction can be carried out via very facile route with very simple and moderate reaction conditions.

We claim:
1. An antioxidant and antiozonant compound of formula 1

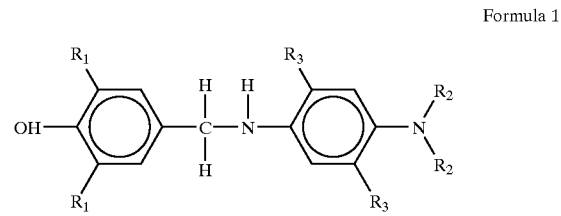

Formula 1 wherein $R_1$ is tert-butyl and $R_2$ and $R_3$ are the same or different and are $C_1$ to $C_8$ linear or branched alkyl.

2. A process for preparation of a compound of formula 1

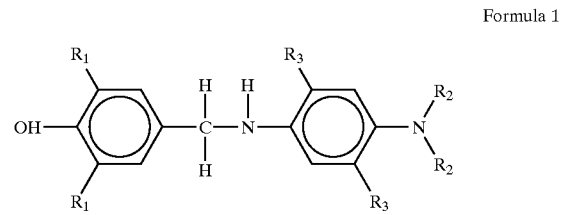

Formula 1 wherein $R_1$ is tert-butyl and $R_2$ and $R_3$ are the same or different and are $C_1$ to $C_8$ linear or branched alkyl which comprises the steps of a) dissolving a compound of formula 3

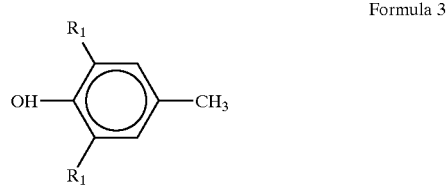

Formula 3 wherein $R_1$ is tert-butyl, with bromine in a non polar organic solvent at a temperature in the range of 80 to 95° C. for a period of 4 to 7 hours, b) evaporating the solvent under reduced pressure to obtain a compound of formula 2

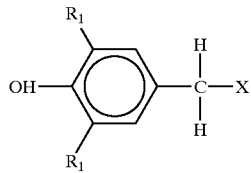

Formula 2 wherein $R_1$ is a tertiary butyl group and X is Br, c) reacting the compound of Formula 2 with compound of formula 4

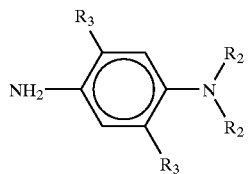

Formula 4 wherein $R_2$ and $R_3$ are the same or different and are $C_1$ to $C_8$ linear or branched alkyl in the presence of an organic solvent using a mild base at a temperature in the range of 80 to 95° C. for a period of 4 to 7 hours, d) bringing the reaction mixture to room temperature, e) separating the organic layer to obtain the compound of formula I.

3. The process as claimed in claim 2 wherein the non-polar organic solvent used for dissolving the compound of formula 3 is a chlorinated solvent.

4. The process as claimed in claim 3 wherein the chlorinated solvent is selected from the group consisting of carbon tetrachloride, chloroform, chlorobenzene and dichloromethane.

5. The process as claimed in claim 2 wherein the compound of formula 4 is selected from the group consisting of N,N-dimethyl-para-phenylene diamine, N,N-diethyl-para-phenylene diamine, 2,5-dimethyl-para-phenylene diamine and 2,5-diethyl-para-phenylene diamine.

6. The process as claimed in claim 2 wherein the organic solvent used in step c) is tetrahydrofuran (THF).

7. The process as claimed in claim 2 wherein the mild base added in step c) is selected from the group consisting of carbonates and bicarbonates of alkali metals.

8. The process as claimed in claim 7 wherein the carbonates and bicarbonates of alkali metals are selected from the group consisting of potassium carbonate, sodium carbonate, potassium bicarbonate and sodium bicarbonate.

9. The process as claimed in claim 2 wherein the compound of formula 1 is concentrated by solvent evaporation under reduced pressure and purified by silica gel chromatography.

* * * * *